United States Patent
Eliu et al.

(10) Patent No.: US 7,931,696 B2
(45) Date of Patent: Apr. 26, 2011

(54) CATIONIC DYES

(75) Inventors: Victor Paul Eliu, Lörrach (DE); Beate Fröhling, Grenzach-Wyhlen (DE); Dominique Kauffmann, Illzach (FR)

(73) Assignee: BASF SE Ludwigshafen (DE)

( * ) Notice: Subject to any disclaimer, the term of this patent is extended or adjusted under 35 U.S.C. 154(b) by 0 days.

(21) Appl. No.: 12/520,887

(22) PCT Filed: Jan. 22, 2008

(86) PCT No.: PCT/EP2008/050666
§ 371 (c)(1),
(2), (4) Date: Nov. 18, 2009

(87) PCT Pub. No.: WO2008/092771
PCT Pub. Date: Aug. 7, 2008

(65) Prior Publication Data
US 2010/0058545 A1 Mar. 11, 2010

(30) Foreign Application Priority Data
Jan. 31, 2007 (EP) .................... 07101501

(51) Int. Cl.
*A61Q 5/10* (2006.01)
*C07D 333/00* (2006.01)

(52) U.S. Cl. .............. 8/405; 8/455; 8/462; 132/202; 132/208; 549/53

(58) Field of Classification Search ............ 8/405, 455, 8/462; 132/202, 208; 549/53
See application file for complete search history.

(56) References Cited

U.S. PATENT DOCUMENTS
4,714,763 A * 12/1987 Theodoropulos ........... 544/31
6,251,687 B1 6/2001 Buechler
7,563,289 B2 7/2009 Eliu et al.
2003/0225147 A1 12/2003 Chu et al.
2004/0029875 A1 2/2004 Fauchere et al.
2009/0100610 A1 4/2009 Cremer et al.
2009/0130045 A1 5/2009 Cremer et al.
2009/0151091 A1 6/2009 Cremer et al.

FOREIGN PATENT DOCUMENTS
| EP | 0319620 | 6/1989 |
| EP | 1477158 | 11/2004 |
| WO | 9501772 | 1/1995 |
| WO | 0039077 | 7/2000 |

OTHER PUBLICATIONS
STIC Search Report dated Dec. 22, 2010.*

* cited by examiner

*Primary Examiner* — Eisa B Elhio
(74) *Attorney, Agent, or Firm* — Shiela A. Loggins

(57) ABSTRACT

Disclosed are dyes of formula

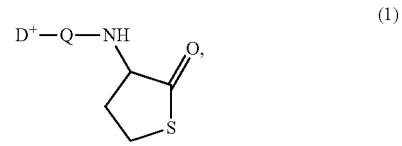

(1)

wherein

D is the radical of anthraquinone, acridine, azo, azomethine, hydrazomethine, benzodifuranone, coumarine, diketopyrrolopyrrol, dioxaxine, diphenylmethane, formazane, indigoid, indophenol, naphtalimide, naphthaquinone, nitroaryl, merocyanine, methine, oxazine, perinone, perylene, pyrenequinone, phtalocyanine, phenazine, quinoneimine, quinacridone, quinophtalone, stilbene, styryl, triphenylmethane, xanthene, thiazine dye and thioxanthene dye;

and Q is defined herein.

17 Claims, No Drawings

CATIONIC DYES

The present invention relates to cationic dyes, compositions thereof, and to their use for the dyeing of organic materials, such as keratin fibers, wool, leather, silk, cellulose or polyamides, especially keratin-containing fibers, cotton or nylon, and preferably hair, more preferably human hair.

It is known, for example, from WO 95/01772 that cationic dyes can be used for the dyeing of organic material, for example keratin, silk, cellulose or cellulose derivatives, and also synthetic fibers, for example polyamides. Cationic dyes exhibit very brilliant shades. A disadvantage is their unsatisfactory fastness to washing.

The technical problem is to provide dyes that are distinguished by deep dying having good fastness properties with respect to washing, light, shampooing and rubbing.

Accordingly, the present invention relates to cationic hair dyes of formula

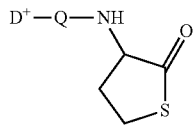

D is the radical of anthraquinone, acridine, azo, azomethine, hydrazomethine, benzodifuranone, coumarine, diketopyrrolopyrrol, dioxaxine, diphenylmethane, formazane, indigoid, indophenol, naphtalimide, naphthaquinone, nitroaryl, merocyanine, methine, oxazine, perinone, perylene, pyrenequinone, phtalocyanine, phenazine, quinoneimine, quinacridone, quinophtalone, stilbene, styryl, triphenylmethane, xanthene, thiazine dye and thioxanthene dye;

Q is $C_1$-$C_{30}$alkylene, —$C_2$-$C_{12}$alkenylene, —$C_5$-$C_{10}$arylene-, —$C_5$-$C_{10}$cycloalkylene- or —$C_1$-$C_{10}$alkylene($C_5$-$C_{10}$arylene)- which may be interrupted and/or terminated at one or both ends by one or more than one —O—, —S—, —N=, —N($R_1$)—, $SO_2$, —($CH_2CH_2$—O)$_{1-5}$—, —($CH_2CH_2CH_2$—O)$_{1-5}$—, —C(O)—$C_1$-$C_{12}$alkenylene, —C(O)O—, —OCO—,

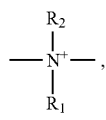

—CON($R_1$)—, —C(N$R_1R_2$)$_2$—, —($R_1$)NC(O)—, —CS$R_1$— or an optionally substituted, saturated or unsaturated, fused or non-fused aromatic or nonaromatic (hetero)cyclic) bivalent radical optionally comprising at least one heteroatom; —O—; —S—; —N($R_1$)—; $SO_2$; —($CH_2CH_2$—O)$_{1-5}$—; —C(O)—; —C(O)—$C_1$-$C_{12}$alkenylene; —C(O)O—, —OCO—;

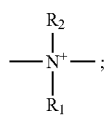

—CON($R_1$)—; —C(N$R_1$, $R_2$)$_2$—; —($R_1$)NC(O)—; CS$R_1$; saturated or unsaturated, fused or non-fused aromatic or non-aromatic bivalent radical optionally comprising at least one heteroatom; which is optionally substituted by $C_1$-$C_{30}$alkyl, $C_1$-$C_{30}$alkoxy, —$C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or $D^+$;

$R_1$ and $R_2$ independently from each other are hydrogen; or unsubstituted or substituted, straight-chain or branched, monocyclic or polycyclic, interrupted or uninterrupted $C_1$-$C_{14}$alkyl; $C_1$-$C_{14}$ hydroxyalkyl; $C_1$-$C_{14}$ aminoalkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl).

Preferably in formula (1)

D is the radical of anthraquinone, acridine, azo, azomethine, hydrazomethine, benzodifuranone, coumarine, diketopyrrolopyrrol, dioxaxine, diphenylmethane, formazane, indigoid, indophenol, naphtalimide, naphthaquinone, nitroaryl, merocyanine, methine, oxazine, perinone, perylene, pyrenequinone, phtalocyanine, phenazine, quinoneimine, quinacridone, quinophtalone, stilbene, styryl, triphenylmethane, xanthene, thiazine dye and thioxanthene dye;

Q is —$C_2$-$C_{12}$alkenylene, —$C_5$-$C_{10}$arylene-, —$C_5$-$C_{10}$cycloalkylene- or —$C_1$-$C_{10}$alkylene($C_5$-$C_{10}$arylene)- which may be interrupted by one or more than one —O—, —S—, —N$R_3$— or $SO_2$; —($CH_2CH_2$—O)$_{1-5}$—; —C(O)—; —C(O)—$C_1$-$C_{12}$alkenylene; —C(O)O—; —OCO—; —N($R_1$)—;

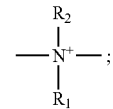

—CON($R_1$)—; —C(N$R_1R_2$)$_2$; —($R_1$)NC(O)—; —CS$R_1$—; —O—; —S—; —CS—; —S(O)—; or —S(O)$_2$—; and $R_1$, $R_2$ and $R_3$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl).

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecyl, dodecyl or tetradecyl.

$C_2$-$C_{12}$alkylene is for example methylene, ethylene, propylene, isopropylene, n-butylene, sec-butylene, tert-butylene, n-pentylene, 2-pentylene, 3-pentylene or 2,2'-dimethylpropylene, n-hexylene, n-octylene, 1,1',3,3'-tetramethylbutylene, 2-ethylhexylene, nonylene, decylene, undecylene or dodecylene.

Alkylene may be straight-chain, branched, or, from $C_5$alkyl upwards, monocyclic or polycyclic, and may be interrupted by hetero atoms, such as such as O, S, —CO—, N, NH, N$R_a$, —OCO—, —CO(O$R_a$)—, —CON$R_a$—, —($R_b$)NC(O)—; for example $C_1$-$C_{10}$alkylene may be a reissue such as: —$CH_2CH_2$—O—$CH_2CH_2$—O—$CH_2CH_2$—, —$CH_2CH_2$—O—$CH_2CH_2$—, —$CH_2CH_2$—O—$CH_2$—, —$CH_2$—O—$CH_2$—, —$CH_2CH_2$—$CH_2CH_2$—O—$CH_2$—$CH_2$—, —$CH_2CH_2$—CH(N($CH_3$)$_2$)—$CH_2$—$CH_2$—, $CH_2$—$NH_2$—$CH_2$—$CH_2$—, —$CH_2CH_2$—NH—$CH_2CH_2$—, —$CH_2CH_2$—N$CH_3$—$CH_2CH_2$—, —CO—$CH_2$—, —$CH_2CO$—, —$CH_2CH_2$—NHCO—$CH_2CH_2$—, —$CH_2CH_2$—CONH—$CH_3$—$CH_2CH_2$—, —$CH_2CH_2$—N$CH_3$CO—$CH_2CH_2$—, —$CH_2CH_2$—CON$CH_3$—$CH_3$—

CH$_2$CH$_2$—, —CH$_2$—NHCO—CH$_2$CH$_2$—, —CH$_2$CH$_2$—NHCO—CH$_2$—, —CH$_2$CH$_2$—CONH—CH$_2$— or —CH$_2$—CONH—CH$_2$CH$_2$—.

R$_a$ and R$_b$ independently from each other are hydrogen; C$_1$-C$_{12}$alkyl, which may be substituted by one or more C$_1$-C$_5$alkyl, C$_1$-C$_5$-alkoxy or hydroxyl; —(CO)—H; —(CO)—C$_1$-C$_5$alkyl; phenyl or phenyl-C$_1$-C$_4$alkyl, wherein the phenyl moiety may be substituted by one or more C$_1$-C$_5$alkyl, C$_1$-C$_5$alkoxy, halogen, —NH$_2$, mono-C$_1$-C$_5$alkylamino, di-C$_1$-C$_5$alkylamino, —NO$_2$, carboxy or hydroxyl.

C$_5$-C$_{10}$cycloalkylene is for example cyclopentylene, cyclohexylene, cycloheptylene, cyclooctylene, cyclononylene or cyclodecylene.

C$_5$-C$_{10}$arylene is for example phenylene or naphthylene.

Aryl-alkylene is for example C$_5$-C$_{10}$aryl-C$_1$-C$_{10}$alkylene.

Alkyl-arylene is for example C$_1$-C$_{10}$alkyl-C$_5$-C$_{10}$arylene.

"Anion" denotes, for example, an organic or inorganic anion, such as halide, preferably chloride and fluoride, sulfate, hydrogen sulfate, phosphate, boron tetrafluoride, carbonate, bicarbonate, oxalate or C$_1$-C$_8$alkyl sulfate, especially methyl sulfate or ethyl sulfate; anion also denotes lactate, formate, acetate, propionate or a complex anion, such as the zinc chloride double salt.

The anion is especially a halide, preferably chloride, bromide or fluoride, sulfate, hydrogen sulfate, benzenesulfonate, tosylate, methyl sulfate, ethyl sulfate, phosphate, formate, acetate or lactate.

The anion is more especially fluoride, chloride, bromide, methyl sulfate, ethyl sulfate, formate or acetate.

Preferred are dyes of formula (1), wherein

D is selected from a nitroaryl, an anthraquinone, a naphthoquinone, a pyrenequinone, a phathylocyanine, a formazane, a methin, an azomethine, a dioxaine, a phenazine, an azo, an indophenol, a stilbene, a triphenylmethane, a xanthene, a thioxanthene and a direct dye; and more preferably wherein D is a cationic direct dye.

Even more preferred are dyes of formula (1), wherein

D is a radical of formula

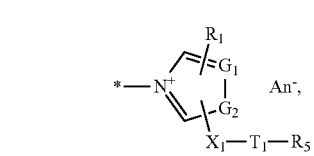
(1a)

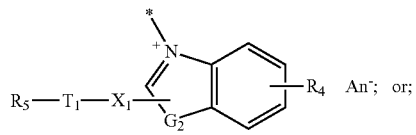
(1b)

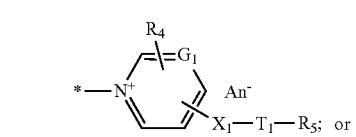
(1c)

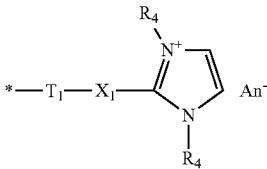
(1d)

X$_1$ is a bivalent radical selected from —N=N—; —CR$_8$=N—; —N=CR$_8$—; —NR$_8$—N=CR$_9$—; and —R$_8$C=N—NR$_9$—;

T$_1$ is a bivalent radical of a substituted or unsubstituted aromatic or heteroaromatic compound;

G$_1$ is N; or a radical CR$_{10}$;

G$_2$ is —O—; or —S—;

R$_4$ and R$_5$ independently from each other are hydrogen; halogen; C$_1$-C$_{16}$alkyl, which may be interrupted with heteroatoms; phenyl; a carboxylic acid radical; a sulfonic acid radical; hydroxy; nitrile; C$_1$-C$_{16}$alkoxy; (poly)-hydroxy-C$_2$-C$_4$-alkoxy; halogen; SO$_2$NR$_6$R$_7$; SR$_6$; NR$_6$R$_7$; OR$_6$; SO$_2$; COOR$_6$; NR$_6$COR$_7$; or CONR$_6$;

R$_6$ and R$_7$ independently from each other are hydrogen; C$_1$-C$_{12}$alkyl, which may be substituted by one or more C$_1$-C$_5$alkyl, C$_1$-C$_5$-alkoxy or hydroxyl; —(CO)—H; —(CO)—C$_1$-C$_5$alkyl; phenyl or phenyl-C$_1$-C$_4$alkyl, wherein the phenyl moiety may be substituted by one or more C$_1$-C$_5$alkyl, C$_1$-C$_5$alkoxy, halogen, —NH$_2$, mono-C$_1$-C$_5$alkyl-amino, di-C$_1$-C$_5$alkylamino, —NO$_2$, carboxy or hydroxy;

R$_8$ and R$_9$ independently from each other are hydrogen; C$_1$-C$_{14}$alkyl; C$_2$-C$_{14}$alkenyl; C$_5$-C$_{10}$aryl; C$_1$-C$_{10}$alkyl-C$_5$-C$_{10}$aryl; or C$_5$-C$_{10}$aryl-C$_1$-C$_{10}$alkyl;

R$_{10}$ is hydrogen; C$_1$-C$_{14}$alkyl; C$_2$-C$_{14}$alkenyl; C$_6$-C$_{10}$aryl; C$_5$-C$_{10}$aryl-(C$_1$-C$_{10}$alkyl); or —C$_1$-C$_{10}$alkyl(C$_5$-C$_{10}$aryl); and An is an anion.

Most preferred are dyes of formula (1), wherein

D is a radical of

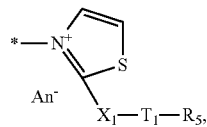
(1a$_1$)

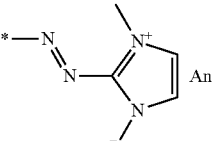
(1a$_2$)

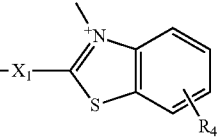
(1b$_1$)

-continued

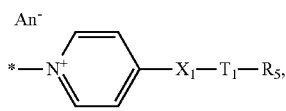
(1c₁)

wherein
$X_1$, $T_1$ $R_4$, $R_5$ and An are defined as above.

Preferred are dyes of formula (1), wherein

Q is a bivalent radical of formula (1a) -(T)$_t$(Z)$_z$—,

T is a radical selected from saturated or unsaturated, linear or branched —$C_1$-$C_{12}$alkylene; —C(O)—; —(CH$_2$CH$_2$—O)$_{1-5}$—; —(CH$_2$CH$_2$CH$_2$—O)$_{1-5}$—; —C(O)O—; —OC(O)—; —N(R$_1$)—; —CON(R$_1$)—; —(R$_1$)NC(O)—; —O—; —S—; —S(O)—; —S(O)$_2$—; —S(O)$_2$—N(R$_1$)—; and —N$^+$(R$_1$)(R$_2$)—;

Z is —(CH$_2$)$_2$—SO$_2$—; —CH$_2$—CHR—CO—NR'—; or a biradical of formula

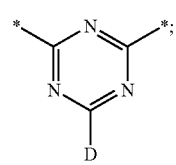
(1b)

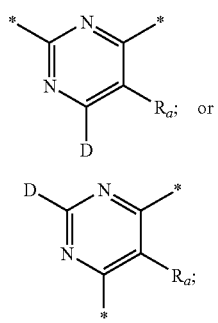
(1c)
(1d)

R and R' independently from each other are hydrogen; or $C_1$-$C_6$alkyl;

D is $R_a$; $D_1^{a+}$; or $D_2^{b+}$;

a and b independently from each other are 1, 2 or 3;

$R_a$ is chlorine or fluorine, $R_1$ is unsubstituted or substituted $C_1$-$C_6$-alkoxy, $C_1$-$C_6$-alkylamino, $C_6$-$C_{10}$-aryloxy or $C_6$-$C_{10}$-arylamino; and t and z, independently from each other are 0; or 1; with the proviso that at least one of t or z is 1.

Most preferred are of formula (1), wherein $X_1$ is a bivalent radical selected from —N=N—; —CR$_8$=N—; and —N=CR$_8$—;

$T_1$ is phenylene;

$R_5$ is NR$_6$R$_7$; OR$_6$; or SO$_2$;

$R_6$ and $R_7$ independently from each other are hydrogen; or $C_1$-$C_{12}$alkyl, which may be substituted by one or more hydroxyl; and $R_8$ is hydrogen; or $C_1$-$C_{14}$alkyl.

The most preferred dyes according to the present invention correspond to formula

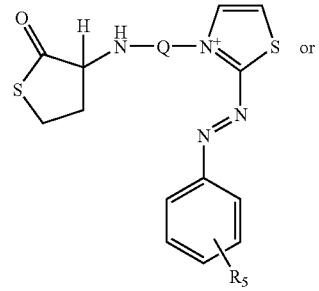
(2a)

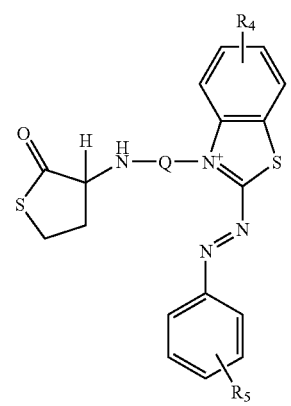
(2b)

wherein
Q is $C_1$-$C_{30}$alkylene; $C_2$-$C_{12}$alkenylene, —$C_5$-$C_{10}$arylene-, —C(O)—; or —C(O)—$C_2$-$C_{12}$alkenylene;

$R_4$ is hydrogen; $C_1$-$C_{16}$alkyl; or $C_1$-$C_{16}$alkoxy;

$R_5$ is NR$_6$R$_7$; and $R_6$ and $R_7$ independently from each other are hydrogen; or $C_1$-$C_{12}$alkyl, which may be substituted by one or more hydroxyl; and to formula

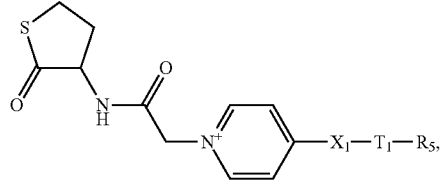
(3)

wherein
$X_1$ is a bivalent radical selected from —N=N—; —CR$_8$=N—;

$R_5$ is NR$_6$R$_7$;

$R_8$ is hydrogen; or $C_1$-$C_{14}$alkyl; and $R_6$ and $R_7$ from each other are hydrogen; $C_1$-$C_{12}$alkyl; or phenyl; and to formula

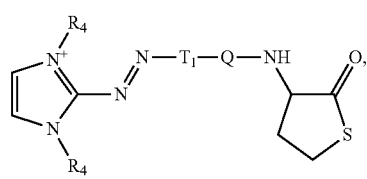
(4)

wherein
T₁ is a bivalent radical of an substituted or unsubstituted aromatic compound;
Q is —$C_2$-$C_{12}$alkenylene, which may be interrupted by one or more than one —$NR_3$—;
$R_3$ is hydrogen; or $C_1$-$C_{14}$alkyl; and
$R_4$ is hydrogen; or $C_1$-$C_{16}$alkyl.
Examples of the dyes of formula (1) are listed in the Table 1 below:
TABLE 1
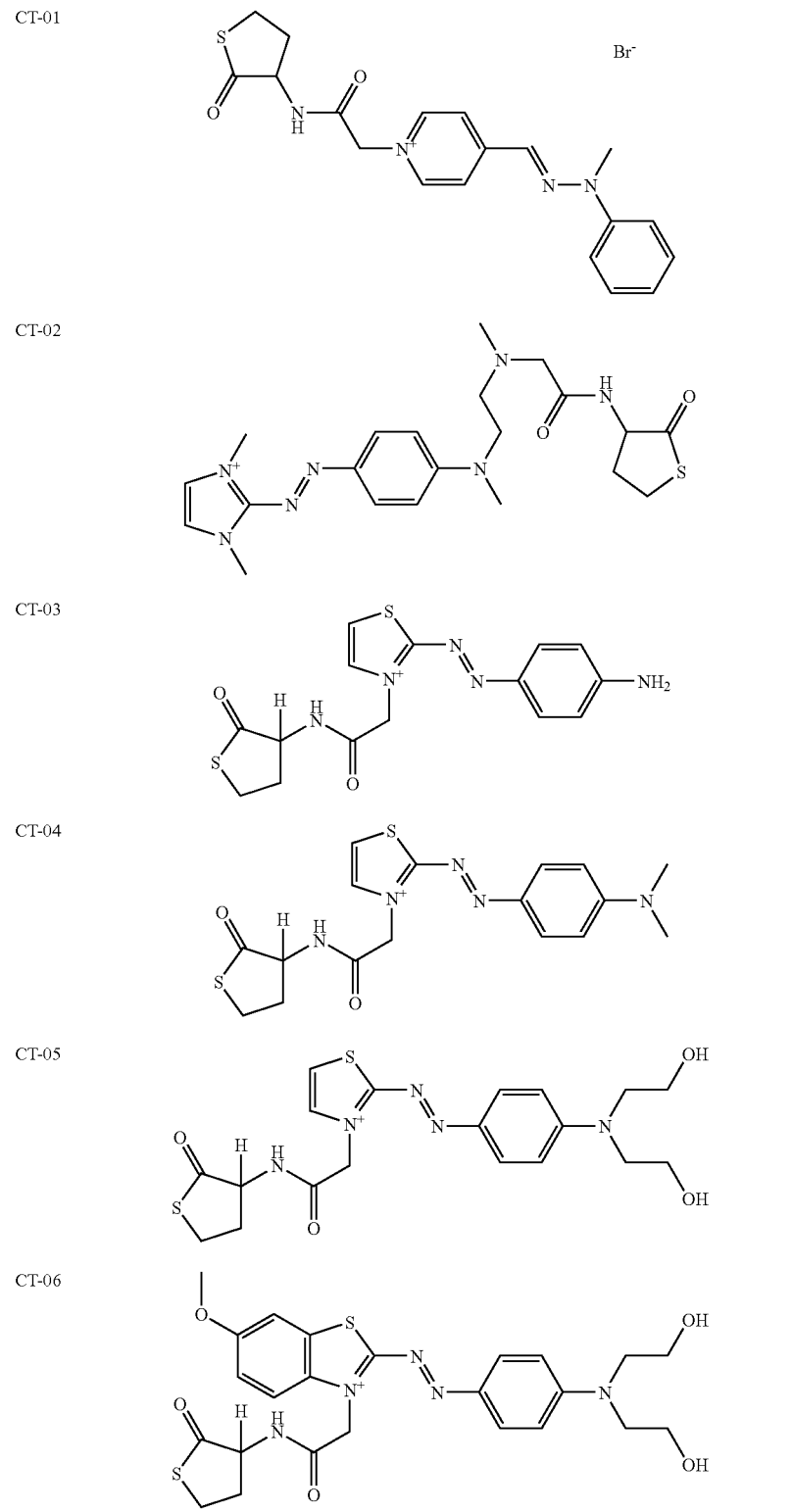

TABLE 1-continued

CT-07

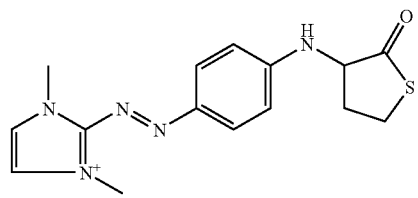

CT-08

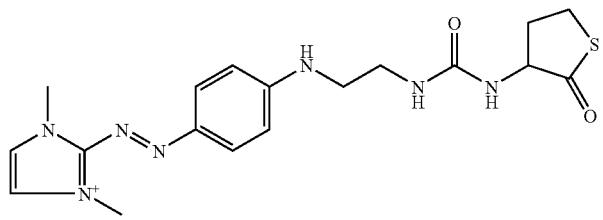

CT-09

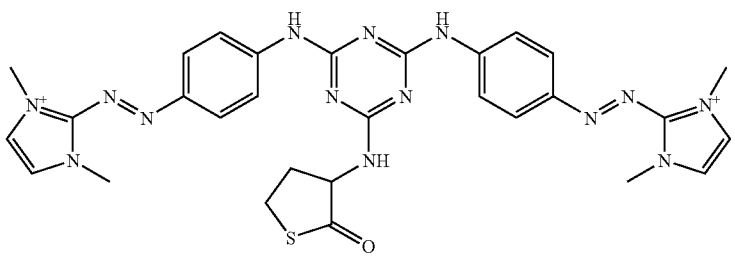

All compounds of the present invention mentioned above can also exist as hydrates or solvates.

A further embodiment of the present invention relates to processes for the preparation of the dyes of formula (1).

Generally, the process comprises the reacting of dye intermediates with 3-amino-dihydro-thiophenone, which is a cyclic thioderivative according to the following reaction scheme:

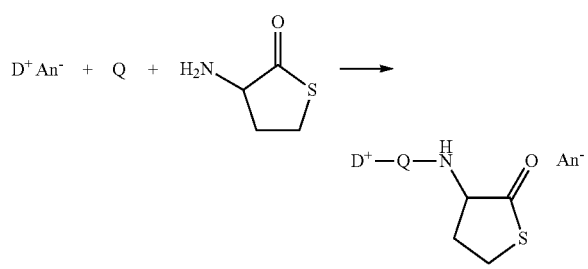

The reaction is generally initiated by contacting, for example by mixing together the starting compounds or by dropwise addition of one starting compound to the other.

Customary, the temperature is in the range of 263-363. K, preferably in the range of 263-330 K during the mixing of the starting compounds.

The reaction time is generally dependent on the reactivity of the starting compounds, on the selected reaction temperature and on the desired conversion. The reaction time is usually in the range from 1 h to 3 days.

The selected reaction pressure is generally in the range from 10 kPa to 1 MPa, especially from 50 kPa to 150 kPa, and is more especially atmospheric pressure.

Preferably the reaction is carried out in the presence of a catalyst.

The molar ratio of compound of formula (1b) to the catalyst is generally selected in the range from 10:1 to 1:5, especially in the range from 10:1 to 1:1.

Preferred are acid catalysts, HA and Lewis acids like $Ag^+$ or base catalysts as tertiary nitrogen bases.

In addition, the reaction may be carried out with or without a solvent, but is preferably carried out in the presence of a solvent, preferably organic solvents or solvent mixtures.

Preferred solvents are alcohols like methanol, ethanol, propanol, 2-propanol or butanol; nitriles like acetonitril or propionitril; amides like dimethylformamide, dimethylacetamide or N-methylpyrolidone; halogenated hydrocarbons like chloroform, methylenechloride, trichloro-ethylene or chlorobenzene; or other solvents like dimethylsulfoxide or water or mixtures of the mentioned solvents.

The product prepared according to the process of the present invention may advantageously be worked up and isolated, and if desired be purified.

Customary, the work up starts by decreasing the temperature of the reaction mixture in the range from 350 to 273 K, especially in the range from 320 to 273 K.

It may be advantageous to decrease the temperature slowly over a period of several hours.

In general, the reaction product is filtered off and subsequently dried.

Filtration is normally carried out in standard filtering equipment, for example Büchner funnels, filter presses, pressurised suction filters, preferably in vacuo.

The temperature for the drying is dependent on the pressure applied. Drying is usually carried out in vacuo at 50-200 mbar.

The drying is usually carried out at a temperature in the range from 313 to 363 K, especially from 323 to 353 K, and more especially in the range from 328 to 348 K.

Advantageously the product is purified by recrystallisation after isolation.

The dyes of formula (1) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing.

Generally, hair dyeing agents on a synthetic base may be classified into three groups:
temporary dyeing agents
semipermanent dyeing agents, and
permanent dyeing agents.

The multiplicity of shades of the dyes can be increased by combination with other dyes.

Therefore the dyes of formula (1) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1) may be used in combination with at least one single direct dye different from the dyes of formula (1).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

Furthermore, the dyes of formula (1) may be combined with at least one cationic azo dye, for example the compounds disclosed in GB-A-2 319 776 as well as the oxazine dyes described in DE-A-299 12 327 and mixtures thereof with the other direct dyes mentioned therein.

The dyes of formula (1) may also be combined with acid dyes, for example the dyes which are known from the international names (Color index), or trade names.

The dyes of formula (1) may also be combined with uncharged dyes.

Furthermore, the dyes of formula (1) may also be used in combination with oxidation dye systems.

Furthermore, autooxidizable compounds may be used in combination with the dyes of formula (1).

The dyes of formula (1) may also be used in combination with naturally occurring dyes.

Furthermore, the dyes of formula (1) may also be used in combination with capped diazotised compounds.

Suitable diazotised compounds are for example the compounds of formula (1)-(4) in WO 2004/019897 (bridging gages 1 and 2) and the corresponding water-soluble coupling components (I)-(IV) as disclosed in the same reference on p. 3 to 5.

The present invention also relates to formulations, which are used for the dyeing of organic materials, preferably keratin-containing fibers, and most preferably human hair, comprising at least one dye of formula (1).

Preferably the dyes of formula (1) are incorporated into the composition for treating organic material, preferably for dyeing in amounts of 0.001-5% by weight (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

The dyeing compositions of the present invention are applied on the hair in a temperature range of 25 to 200, preferably 18 to 80, and most preferably from 20 to 40° C.

One preferred embodiment of the present invention relates to the formulation of dyes, wherein the dyes of formula (1) are in powder form.

Powder formulations are preferably used if stability and/or solubility problems as for example described in DE 197 13 698, p. 2, l. 26 to 54 and p. 3, l. 51 to p. 4, l. 25, and p. 4, l. 41 to p. 5 l. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or camomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

If the dyes of formula (1) are used together with oxidation dyes and/or the addition salts thereof with an acid, they may be stored separately or together. Preferably the oxidation dyes and the direct dyes which are not stable to reduction are stored separately.

The dyes of formula (1) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention:-non-ionic polymers cationic polymers, acrylamide/dimethyldiallylammonium chloride copolymers, diethyl-sulfate-quaternised dimethylaminoethyl methacrylate/vinyl-pyrrolidone copolymers, vinylpyrrolidone/imidazolinium methochloride copolymers; quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilisers, anti-dandruff active ingredients, substances for adjusting the pH value, panthenol, pantothenic acid, allantoin, pyrrolidone-carboxylic acids and salts thereof, plant extracts and vitamins, cholesterol;-light stabilisers and UV absorbers, consistency regulators, fats and waxes, fatty alkanolamides, polyethylene glycols and polypropylene glycols having a molecular weight of from 150 to 50 000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one dye of formula (1) and
(b) leaving the fiber to stand and then rinsing the fiber.

The dyes of formula (1) are suitable for all-over dyeing of the hair, that is to say when dyeing the hair on a first occasion, and also for re-dyeing subsequently, or dyeing of locks or parts of the hair.

The dyes of formula (1) are applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1), a base and an oxidizing agent.

A preferred embodiment for dyeing keratin-containing fibers, in particular human hair, with a dye of formula (1) and an oxidizing agent, comprises
$a_1$) treating the keratin-containing fiber with the oxidizing agent, which optionally contains at least one dye of formula (1),
$b_1$) treating the keratin-containing fiber with an oxidizing agent free composition, which optionally contains at least one dye of formula (1); or alternatively
$a_2$) treating the keratin-containing fiber with an oxidizing agent free composition, which optionally contains at least one dye of formula (1);
$b_2$) treating the keratin-containing fiber with an oxidizing agent, which optionally contains least one dye of formula (1),
with the proviso that at least in one of the process steps $a_1$), $a_2$), $b_1$) or $b_2$) a dye of formula (1) is present.

In general, the oxidizing agent containing composition is left on the fiber for 0 to 45 minutes, in particular for 15 to 30 minutes at 15 to 45° C.

The oxidizing agent free composition usually comprises customary adjuvants and additives. Preferred are those, which are described in German Patent Application, in col 3, I. 17 to I. 41.

In general, the dye of formula (1) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1) which are stable to reduction can be stored together with the oxidizing agent free compositions and may be applied as a single composition.

Advantageously the compositions comprising a dye of formula (1) which are not stable to reduction are prepared with the oxidizing agent free composition just before the dyeing process.

In a further embodiment, the dye of formula (1) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkaline earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

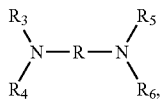

wherein
R is a propylene residue, which may be substituted with OH or $C_1$-$C_4$alkyl,
$R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations-comprising the dyes of formula (1) on the keratin-containing fiber, preferably the hair is by using a multi-compartment dyeing device or "kit" or any other multi-compartment packaging system, as described for example in WO 97/20545 on p. 4, l. 19 to l. 27.

Generally the hair is rinsed after treatment with the dyeing solution and/or permanent-wave solution.

A further preferred embodiment of the present invention relates to a method of dyeing hair with oxidative dyes, which comprises
a. mixing at least one dye of formula (1) and optionally at least one coupler compound and at least one developer compound, and an oxidizing agent, which optionally contains at least one further dye, and
b. contacting the keratin-containing fibers with the mixture as prepared in step a.

For adjusting the pH-value organic or inorganic acids, as for example described in DE 199 59 479, col 3, l. 46 to l. 53 are suitable.

Furthermore, the present invention relates to a process of dyeing of keratin-containing fibers of the dyes of formula (1) with autooxidable compounds and optionally further dyes.

The process comprises
a. mixing at least one autooxidable compound and at least one developer compound and at least one dye of formula (1) and optionally further dyes, and
b. treating the keratin-containing fiber with the mixture prepared in step a.

Furthermore, the present invention relates to a process for dyeing keratin-containing fibers
with the dyes of formula (1) and capped diazotised compounds, which comprises,
a. treating the keratin-containing fibers under alkaline conditions with at least one capped diazotised compound and a coupler compound, and optionally a developer compound and optionally an oxidizing agent, and optionally in the presence of a further dye, and optionally with at least one dye of formula (1), and
b. adjusting the pH in the range of 6 to 2 by treatment with an acid, optionally in the presence of a further dye, and optionally at least one dye of formula (1), with the proviso that at least in one step a. or b. at least one dye of formula (1) is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1) and at least one acid dye.

The following Examples serve to illustrate the processes for dyeing without limiting the processes thereto. Unless specified otherwise, parts and percentages relate to weight. The amounts of dye specified are relative to the material being coloured.

n the dyeing is carried out in presence of a reducing agent.

PREPARATION EXAMPLES A

Example A1

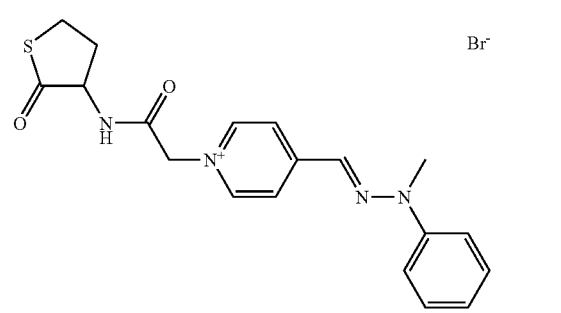

(101)

1. Formation of the Hydrazone 14 g sulfuric acid are added to 42 g water and cooled to 20° C.

Then 24 g N-methyl-phenyl hydrazine (100%) are added with stirring.

24.5 g 4-pyridine-aldehyde are dropped in during 15 min and stirring is continued for 1 h.

The pH is raised to 2.2 by adding a solution of 36% sodium hydroxide in water.

2.7 g sodium chloride are added at the temperature of 60° C., and one more h stirred at this temperature.

The slurry is separated by filtration, the filter cake dried at 70° C. in vacuum to yield 42 g of an orange powder.

2. Alkylating Agent

A mixture of 52.0 g of racemic 3-amino-dihydro-thiophenone in 120 ml chloroform and 74.1 g pyridine are cooled with stirring to 0° C. and then 58.0 g bromo acetic acid chloride are added in small amounts maintaining the temperature.

After completion of the addition the mixture is left overnight in the refrigerator and the reaction is finished.

The reaction mixture is mixed with a water/chlorhidric acid and ice slurry, the phases are separated, washed with water and dried, the solvent is evaporated to dryness to the product used as such in the following step 3. Alkylation The foregoing hydrazone is dissolved in chloroform by stirring with the equivalent amount of alkylating agent at a temperature of 20° C.

The temperature is maintained at 20° C. during the following 48 h. Crystals separated in the slurry are filtered off.

The product is washed with 50 ml chloroform and dried in vacuum to obtain 59 g of an orange solid product.

The product is recrystallized twice from methanol.

The product is characterized by the following data:
1H-NMR data in deuterated methanol (32 scans)/360 MHz

| 8.564 | d | 6.8 | 2.00 | py |
|-------|---|-----|------|----|
| 8.102 | d | 6.7 | 2.00 | py |
| 7.677 | s |     | 0.994 | hydrazone |
| 7.540 | d | 6.1 | 1.97 | phe |
| 7.414 | t | 6.1 | 2.025 | phe |
| 7.154 | t | 6.4 | 1.005 | phe |
| 5.356 | s |     | 1.72 | methylene |
| 4.750 | q | 12; 7 | 1.00 | thiolactone |
| 3.615 | s |     | 3.05 | me-hydrazone |
| 3.464 | he |    | 1.047 | thiolactone |
| 3.35  | M, | overlaid |  | thiolactone |
| 2.672 | m |     | 1.02 | thiolactone |
| 2.326 | s |     | 0.927 | thiolactone |

Example A2

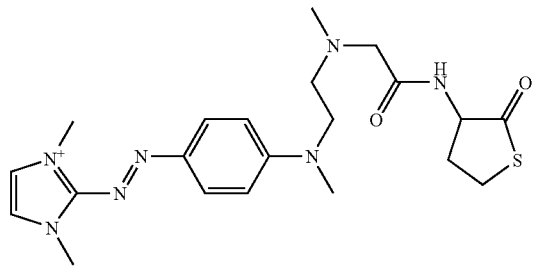

(102)

1. Monoazo 12.4 g 4-fluoroaniline is added to a stirred solution of 25 ml water and 25 ml 32% hydrochloric acid at 295 K.

Then the reaction mixture is cooled to 273K and 19 ml 36% sodium nitrite solution is dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide paper) further amounts of sodium nitrite solution are added.

After this one hour the remaining excess of nitrite is reduced with sulfamic acid.

Then the obtained diazo solution is dropped to a 273 K cold solution of 7.4 g imidazole in 30 ml water, whereby the pH of the solution is maintained in the range of pH 10 to 11 by adding 36% sodium hydroxide solution.

After completing the diazo addition the obtained suspension is warmed up to 295K and the pH is adjusted to 10.5 with 36% sodium hydroxide solution.

After one hour stirring at this pH and temperature the suspension is filtered off and then washed twice with 50 ml water to obtain 55 g of the humid product.

500 ml water are introduced into a reaction vessel, the filter cake from the previous step is added and suspended by stirring. The addition of dimethyl sulphate is started and simultaneously that of sodium hydroxide maintaining the pH at 10-10.3 and the temperature at 25-30° C.

The amount of 3 equivalent of dimethyl sulphate (DMS) are added within ca. 5 h.

It is held for one more hour to finish the hydrolysis of excess of DMS.

The disappearance of DMS is controlled.

Then 100 g sodium chloride are and 50 g potassium chloride are added and cooled to 0° C.

After 16 h the product is separated by filtration and washed with a cold solution of sodium/potassium chloride.

Ca. 20 g cake mole product is obtained with the following formula

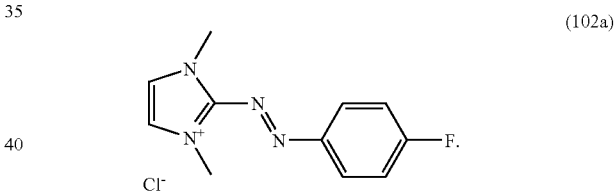

(102a)

19.9 g of N,N'-dimethyl-ethylendiamine is added at 293 K under nitrogen atmosphere with stirring to 120 g isopropanol and the foregoing compound of the formula (102a).

Then the temperature is raised then to 333K and viscosity of the reaction mixture decreases.

The reaction mixture is stirred at this temperature during 25 h.

Then the reaction mass is stirred for 4 h while the temperature is decreased to 295K.

The reaction mass is filtered off and the filter residue is washed with 45 ml isopropanol. Then The material is dried in vacuum to obtain 16 g of product.

2. Alkylating Agent

A mixture of 52.0 g of racemic 3-amino-dihydro-thiophenone as chlorohydrate in 120 ml chloroform and 54.1 g triethylamine are cooled with stirring to 0° C. and then 58.0 g of bromo acetic acid chloride are added in small amounts maintaining the temperature.

After completion of the addition the mixture is left overnight in the refrigerator and the reaction is finished.

The reaction mixture is mixed with a water/chlorhidric acid and ice slurry, the phases are separated, washed with water, dried and the solvent evaporated to dryness the product used as such in the following step.

3. Alkylation

One equivalent of the foregoing monoazo is dissolved by stirring into the solution of the equivalent alkylation agent in chloroform.

The temperature is raised to 60° C. and during the following 20 hours.

Crystals separated in the slurry are filtered off.

The product is washed with 5 ml chloroform and dried in vacuum to obtain 80 g of a dark solid product.

The product is recrystallized twice from methanol.

The product is characterized by the following data: 1H-NMR data in deuterated methanol (32 scans)/360 MHz

| 8.046 | d | 7.3 | 2.00 | phenylene |
| 7.605 | s | | 1.92 | imidazole |
| 7.102 | d | 7.8 | 2.06 | phenylene |
| 4.705 | q | 12; 6 | 0.97 | thiolactone |
| 4.084 | s | | 6.06 | dimethyl |
| 3.86 | t | 6 | 2.02 | methylene |
| 3.595 | s | | 1.982 | methylene |
| 3.26 | | | 3.03 | methyl |
| 2.672 | m | | 1.01 | thiolactone |
| 2.259 | s | | 3.10 | methyl |
| 2.204 | m | | 0.98 | thiolactone |

Example A3

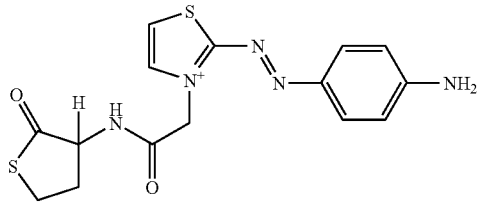

(103)

1. Monoazo 50.0 g 2-amino-thiazol are added to a stirred solution of 135 ml 60% sulfuric acid at 293-310K. Then the reaction mixture is cooled to 273K and 81 ml of a 40% nitrosilsulfuric acid is dropped at such a rate that the temperature of the mixture is maintained in the range of 273 to 276 K by cooling.

After the addition the mixture is stirred for 4 h.

The solution is dropped to a well-stirred water ice mixture (400 g) containing 2.5 g amido-sulfuric acid.

To the obtained diazo solution (at 273K, ice added if need) 45.5 g aniline is dropped.

Then the pH of the solution is raised to the range of 5 to 6 by adding 36% sodium hydroxide solution.

After one hour stirring at this pH and temperature the suspension is filtered off and then washed twice with 50 ml water to obtain 155 g of the humid product.

After drying 90 g monoazo dye is obtained.

2. Alkylating Agent

The same alkylating agent is used as in previous examples.

3. Alkylation

The foregoing monoazo (30 g) is dissolved by stirring into 150 ml methanol.

The equivalent amount of alkylating agent is added. The temperature is raised to 60° C.

The temperature is maintained during the following 30 h.

Crystals separated in the slurry after cooling are filtered off.

The product is washed with 50 ml methanol and dried in vacuum to obtain 49 g of an dark reddish solid product.

The product is recrystallized twice from methanol.

The product is characterized by 1H-NMR Data in deuterated methanol (128 scans)/360 MHz

| 8.244 | d | J = 8.6; | 1.007 | phenylene |
| 7.848 | d | J = 4.2 | 1.00 | thiazol |
| 7.761 | d | J = 8.5 | 1.10 | phenylene |
| 7.500 | d | J = 4.3 | 0.98 | thiazol |
| 6.914 | d | J = 8.6 | 2.00 | phenylene |
| 5.320 | s | | 1.908 | methylene |
| 4.733 | q | 12; 7 | 1.01 | thiolactone |
| 3.426 | He | | 1.02 | thiolactone |
| 3.361 | m | overlaid | 1.01 | thiolactone |
| 2.640 | m | | 1.00 | thiolactone |
| 2.201 | oct | | 1.10 | thiolactone |

Example A4

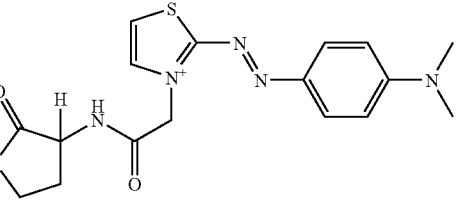

(104)

1. Monoazo 50.0 g 2-amino-thiazol are added to a stirred solution of 135 ml 60% sulfuric acid at 293-310K. Then the reaction mixture is cooled to 273K and 81 ml of a 40% nitrosilsulfuric acid is dropped at such a rate that the temperature of the mixture is maintained in the range of 273 to 276 K by cooling.

After the addition the mixture is stirred for 4 h.

The solution is dropped to a well-stirred water ice mixture (400 g) containing 2.5 g amido-sulfuric acid.

To the obtained diazo solution (at 273K, ice added if need) 60.5 g di-methyl-aniline is dropped.

Then the pH of the solution is raised to the range of 5 to 6 by adding 36% sodium hydroxide solution.

After 1 h stirring at this pH and temperature the suspension is filtered off and then washed twice with 50 ml water to obtain 200 g of the humid product.

After drying 100 g monoazo dye is obtained.

2. Alkylating Agent

The same alkylating agent is used as in previous examples.

3. Alkylation

The foregoing monoazo (28 g) is dissolved by stirring into 150 ml methanol. The equivalent amount of alkylating agent is added.

Temperature is raised to 60° C. and maintained during the following 24 h.

Crystals separated in the slurry after cooling are filtered off.

The product is washed with 50 ml methanol and dried in vacuum to obtain 45 g of a dark violet solid product.

The product is recrystallized twice from methanol.

The product is characterized by 1H-NMR Data in deuterated methanol (128 scans)/360 MHz

| | | | | |
|---|---|---|---|---|
| 8.242 | d | J = 8.6; | 1.007 | phenylene |
| 7.818 | d | J = 4.2 | 1.00 | Thiazol |
| 7.786 | d | J = 8.5 | 1.10 | phenylene |
| 7.505 | d | J = 4.3 | 1.03 | Thiazol |
| 7.273 | d | J = 8.6 | 2.00 | phenylene |
| 5.322 | s | | 1.908 | methylene |
| 4.738 | q | 12; 7 | 1.01 | thiolactone |
| 3.448 | He | | 1.02 | thiolactone |
| 3.34 | m | overlaid | 1.01 | thiolactone |
| 3.27 | s | | 6.05 | methyl |
| 2.364 | m | | 1.00 | thiolactone |
| 2.208 | oct | | 1.10 | thiolactone |

Example A5

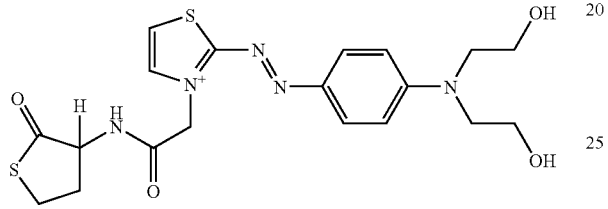

(105)

1. Monoazo 50.0 g 2-amino-thiazol is added to a stirred solution of 135 ml 60% sulfuric acid at 293-310K.

Then the reaction mixture is cooled to 273K and 81 ml of a 40% nitrosilsulfuric acid is dropped at such a rate that the temperature of the mixture is maintained in the range of 273 to 276 K by cooling.

After the addition the mixture is stirred for 4 h.

The solution is dropped to a well-stirred water ice mixture (400 g) containing 2.5 g amido-sulfuric acid.

To the obtained diazo solution (at 273K, ice added if need) 90.5 g di-hydroxyethyl-aniline is dropped.

Then the pH of the solution is raised to the range of 5 to 6 by adding 36% sodium hydroxide solution.

After 1 h stirring at this pH and temperature the suspension is filtered off and then washed twice with 50 ml water to obtain 255 g of the humid product.

After drying 140 g monoazo dye is obtained.

2. Alkylating Agent

A mixture of 52.0 g of racemic 3-amino-dihydro-thiophenone in 120 ml chloroform and 74.1 g pyridine are cooled with stirring to 0° C. and then 58.0 g bromo acetic acid chloride are added in small amounts maintaining the temperature.

After completion of the addition the mixture is left one in the refrigerator and the reaction is finished.

The reaction mixture is mixed with a water/chlorhidric acid and ice slurry, the phases are separated, washed with water, dried, the solvent is evaporated to dryness the product used as such in the following step.

3. Alkylation

The foregoing monoazo (30 g) is dissolved by stirring into 150 ml methanol.

The equivalent amount of alkylating agent is added. The temperature is raised to 60° C. The temperature is maintained at 60° C. during the following 30 h.

Crystals separated in the slurry after cooling are filtered off.

The product is washed with 50 ml methanol and dried in vacuum to obtain 59 g of a dark violet solid product.

The product is recrystallized twice from methanol.

The product is characterized by 1H-NMR Data in deuterated methanol (128 scans)/360 MHz

| | | | | |
|---|---|---|---|---|
| 8.214 | d | J = 8.6; | 1.007 | phenylene |
| 7.871 | d | J = 4.2 | 1.00 | Thiazol |
| 7.781 | d | J = 8.5 | 1.10 | phenylene |
| 7.520 | d | J = 4.3 | 0.98 | Thiazol |
| 7.267 | d | J = 8.6 | 2.00 | phenylene |
| 5.322 | s | | 1.908 | methylene |
| 4.738 | q | 12; 7 | 1.01 | thiolactone |
| 4.000 | T | 6 | 4.05 | methylene |
| 3.913 | t | 6 | 4.05 | methylene |
| 3.448 | He | | 1.02 | thiolactone |
| 3.34 | m | overlaid | 1.01 | thiolactone |
| 2.364 | m | | 1.00 | thiolactone |
| 2.208 | oct | | 1.10 | thiolactone |

Example A6

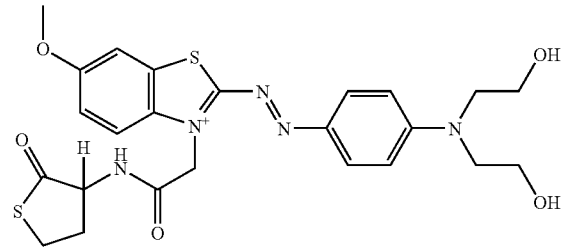

(106)

50.0 g 2-amino-methoxy benzothiazole are added to a stirred solution of 135 ml 60% sulfuric acid at 293-310K.

Then the reaction mixture is cooled to 273K and 61 ml 40% nitrosilsulfuric acid are dropped at such a rate that the temperature of the mixture is maintained in the range of 273 to 276K by cooling. After the addition the mixture is stirred for 4 h.

The solution is dropped to a well-stirred water ice mixture (400 g) containing 2.5 g amidosulfuric acid. To the obtained diazo solution (at 273K ice added if need) 50.5 g dihydroxyethylaniline are dropped. Then the pH of the solution is raised to the range of 5 to 6 by adding 36% sodium hydroxide solution.

After one hour stirring at this pH and temperature the suspension is filtered off and then washed twice with 50 ml water to obtain 15 g of the humid product.

After drying 95 g monoazo dye is obtained.

2. Alkylating Agent

A mixture of 52.0 g of racemic 3-amino-dihydro-thiophenone in 120 ml chloroform and 74.1 g pyridine is cooled with stirring to 0° C. and then 58.0 g of bromo acetic acid chloride are added in small amounts maintaining the temperature.

After completion of the addition the mixture is left one in the refrigerator and the reaction is finished. The reaction mixture i mixed with a water/chlorhidric acid and ice slurry, the phases are separated, washed with water, dried, the solvent is evaporated to dryness the product used as such in the following step.

3. Alkylation

The 39 g foregoing monoazo is dissolved by stirring into the equivalent alkylation solution in 100 ml methanol.

The temperature is raised to 60° C. and maintained during the following 60 h. Crystals separated in the slurry are filtered off.

The product is washed with 50 ml chloroform and dried in vacuum to obtain 59 g of a dark solid product.

The product is recrystallized twice from methanol.

The product is characterized by 1H-NMR Data in deuterated methanol (128 scans)/360 MHz

| 8.214 | d | J = 8.6; | 1.007 | phenylene |
|---|---|---|---|---|
| 7.871 | d | J = 6.2 | 2.00 | benzothiazol |
| 7.781 | d | J = 8.5 | 1.10 | phenylene |
| 7.520 | d | J = 6.3 | 1.98 | benzothiazol |
| 7.267 | d | J = 8.6 | 2.00 | phenylene |
| 5.322 | s |  | 1.908 | methylene |
| 4.738 | q | 12; 7 | 1.01 | thiolactone |
| 4.000 | T | 6 | 4.05 | methylene |
| 3.913 | t | 6 | 4.05 | methylene |
| 3.448 | He |  | 1.02 | thiolactone |
| 3.34 | m | overlaid | 1.01 | thiolactone |
| 2.364 | m |  | 1.00 | thiolactone |
| 2.208 | oct |  | 1.10 | thiolactone |

Example A7

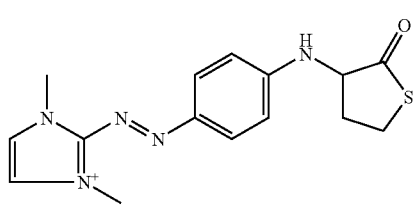
(107)

1. Monoazo 12.4 g 4-fluoroaniline are added to a stirred solution of 25 ml water and 25 ml of 32% hydrochloric acid at 295 K.

Then the reaction mixture is cooled to 273K and 19 ml 36% sodium nitrite solution are dropped at such a rate that the temperature of the mixture is maintained in the range of 273 to 276 K.

After the addition of the sodium nitrite solution the mixture is stirred for 1 h. If no excess of nitrite is detected during 1 h (detection by using a potassium iodide paper) further amounts of sodium nitrite solution are added.

After this 1 h the remaining excess of nitrite is reduced with sulfamic acid.

Then the obtained diazo solution is dropped to a 273K cold solution of 7.4 g imidazole in 30 ml water whereby the pH of the solution is maintained in the range of pH 10 to 11 by adding 36% sodium hydroxide solution.

After completing the diazo addition the obtained suspension is warmed up to 29 K and the pH is adjusted to 10.5 with 36% sodium hydroxide solution.

After one hour stirring at this pH and temperature the suspension is filtered off and then washed twice with 50 ml water to obtain 55 g of the humid product.

500 ml water are introduced into a reaction vessel wherein the filter cake from the previous step is added and suspend by stirring.

The addition of dimethyl sulphate is started and simultaneously that of sodium hydroxide maintaining the pH at 10-10.3 and the temperature at 25-30° C.

The amount of 3 equivalents of dimethyl sulphate (DMS) is added within ca. 5 h.

It is held for 1 h to finish the hydrolysis of excess of DMS.

The disappearance of DMS is controlled.

Then 100 g of sodium chloride and 50 g of potassium chloride are add and cooled to 0° C.

After 16 h the product is separated by filtration and washed with a cold solution of sodium/potassium chloride.

Ca. 20 g cake mole product of formula

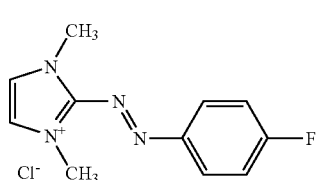
(107a)

are obtained.

20.8 g of racemic 3-amino-dihydro-thiophenone is added at 29 K under nitrogen atmosphere with stirring to 120 g isopropanol and the equivalent amount of triethylamine and the foregoing compound of the formula (107a).

Then the temperature is raised to 333K and viscosity of the reaction mixture decreases.

The reaction mixture is stirred at this temperature during 5 h.

Then the reaction mass is stirred for 4 h while the temperature is decreased to 295K.

The reaction mass is filtered off and the filter residue is washed with 4 ml isopropanol.

Then the material is dried in vacuum to obtain 26 g of product.

The product is characterized by the following data: 1H-NMR data in deuterated chloroform (128 scans)/360 MHz

| 8.046 | d |  | 7.3 | 2.00 | phenylene |
|---|---|---|---|---|---|
| 7.605 | S |  |  | 1.92 | imidazol |
| 7.102 | d |  | 7.8 | 2.06 | phenylene |
| 4.705 | q |  | 12; 6 | 0.97 | thiolacton |
| 4.084 | s |  |  | 12.06 | dimethyl |
| 3.86 | t |  | 6 | 2.02 | methylene |
| 3.595 | s |  |  | 1.982 | methylene |
| 3.26 |  |  |  | 3.03 | methyl |
| 2.672 | m |  |  | 1.01 | thiolactone |
| 2.259 | s |  |  | 3.10 | methyl |
| 2.204 | m |  |  | 0.98 | thiolactone |

Example A8

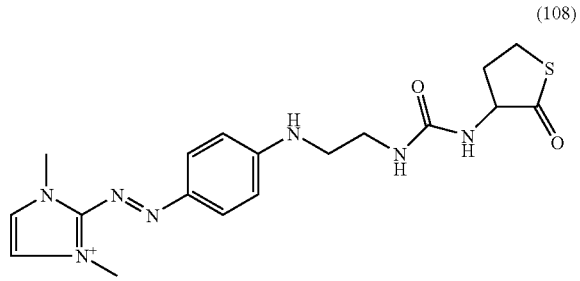
(108)

1. Monoazo 12.4 g 4-fluoroaniline are added to a stirred solution of 2 ml water and 25 ml of 32% hydrochloric acid at 29 K.

Then the reaction mixture is cooled to 273K and 19 ml 36% sodium nitrite solution are dropped at such a rate that the temperature of the mixture is maintained in the range of 273 to 276K. After the addition of the sodium nitrite solution the mixture is stirred for 1 h. If no excess of nitrite is detected during 1 h (detection by using a potassium iodide paper) further amounts of sodium nitrite solution are added.

After 1 h the remaining excess of nitrite is reduced with sulfamic acid.

Then the obtained diazo solution is dropped to a 273K cold solution of 7.4 g imidazole in 30 ml water whereby the pH of the solution is maintained in the range of pH 10 to 11 by adding 36% sodium hydroxide solution.

After completing the diazo addition the obtained suspension is warmed up to 295K and the pH is adjusted to 10.5 with 36% sodium hydroxide solution.

After 1 h stirring at this pH and temperature the suspension is filtered off and then washed twice with 50 ml water to obtain 55 g of the humid product.

500 ml water are introduced into a reaction vessel, the filter cake from the previous step is added and suspended by stirring.

The addition of dimethyl sulphate is started and simultaneously that of sodium hydroxide maintaining the pH at 10-10.3 and the temperature at 25-30° C.

The amount of 3 equivalents of dimethyl sulphate (DMS) is added within ca. 5 h.

It is held for 1 h to finish the hydrolysis of excess of DMS. The disappearance of DMS is controlled.

Then 100 g sodium chloride and 50 g potassium chloride are added and cooled to 0° C.

After 16 h the product is separated by filtration and washed with a cold solution of sodium/potassium chloride.

Ca. 20 g cake mole product of following formula

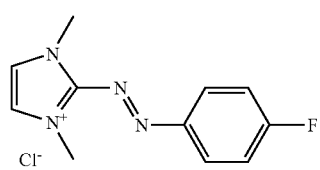
(108a)

are obtained.

2. Amination 19.9 g ethylendiamine are added at 293K under nitrogen atmosphere with stirring to 120 g isopropanol and the foregoing compound of the formula (108a).

Then the temperature is raised to 333K and viscosity of the reaction mixture decreases. The reaction mixture is stirred at this temperature during 25 h.

Then the reaction mass is stirred for 4 h while the temperature is decreased to 295K.

The reaction mass is filtered off and the filter residue is washed with 45 ml isopropanol.

Then the material is dried in vacuum to obtain 26 g of product.

3. Derivatisation 25.9 g of racemic 3-amino-dihydro-thiophenone are added to 120 g toluene at 293K under nitrogen atmosphere with stirring.

Then phosgene is introduced below the surface of the liquid at 333 K.

After completion of the addition the mixture is left 1 h and the reaction is finished.

The reaction mixture is mixed with a water/hydrochloric acid and ice slurry the phases are separated, washed with water, dried and the solvent is evaporated to dryness.

The product is used as such in the following step with the foregoing azo compound.

Both compounds are suspended in acetonitrile.

Then the temperature is raised then to 303K and viscosity of the reaction mixture decreases.

The reaction mixture is stirred at this temperature during 5 h.

The reaction mass is filtered off and the filter residue is washed with 45 ml acetonitrile.

Then the material is dried in vacuum to obtain 36 g of product.

The product is characterized by the following data: 1H-NMR data in deuterated methanol (128 scans)/360 MHz

| | | | | |
|---|---|---|---|---|
| 8.046 | d | 7.3 | 2.00 | phenylene |
| 7.605 | s | | 1.92 | imidazole |
| 7.102 | d | 7.8 | 2.06 | phenylene |
| 4.705 | q | 12; 6 | 0.97 | thiolactone |
| 4.084 | s | | 12.06 | dimethyl |
| 3.86 | t | 6 | 2.02 | methylene |
| 3.595 | s | | 1.982 | methylene |
| 2.672 | m | | 1.01 | thiolactone |
| 2.204 | m | | 0.98 | thiolactone |

B. Application Examples

For the application examples, the following hair types have been used:

blonde hair tress (VIRGIN white hair from IMHAIR Ltd., via G. Verga 8, It 90134 Palermo, Italy)

middle blond hair tress (UNA-Europ. nature hair, color middle blond from Fischbach & Miller, Postfach 1163, 88461 Laupheim, Deutschland)

bleached hair tresses (UNA-Europ. Naturhaar, Farbe weiß-gebleicht from Fischbach & Miller, Postfach 1163, 88461 Laupheim, Deutschland).

The washing fastness of the dyed hair is analyzed by the Grey scale according to Industrial organic pigments by Herbst&Hunger, 2nd ed. engl. S. 61) Nr 10: DIN 54 001-8-1982, "Herstellung and Bewertung der Aenderung der Farbe", ISO 105-A02-1993.

In the following application examples compositions within the below given definitions are used:

Solution 1 (Permanent Lotion, pH 8.2):

Aqua, Ammonium Thioglycolate, Ammonium Bicarbonate, Ethoxydiglycol, Hexylene Glycol, Thioglycolic Acid; Thiolactic Acid, PEG-60 Hydrogenated Castor Oil, Glycine, Etidronic Acid, Isoceteth-20, Polysilicone-9, Styrene/PVP Copolymer, Trideceth-12, Amodimethicone, Cetrimonium Chloride, Ammonium Hydroxide, Polyquaternium-6, Isopropyl Alcohol, Alcohol denat., Simethicone, Parfum.

Solution 2 (Permanent Fixation, pH 3.9):

Based on:

Aqua, Hydrogen Peroxide, Propylene Glycol, Lauryldimonium Hydroxypropyl Hydrolyzed Wheat Protein, PEG-5 Cocamide, Sodium Cocoamphoacetate, Polyquaternium-35, Coco-Betaine, Acetaminophen, Phosphoric Acid, Sodium Chloride, Parfum.

Solution 3 (Dyeing Solution):

0.1% of the dye is dissolved in a 10% solution of a non-ionic surfactant (Plantacare 200UP, Henkel) adjusted to pH 9.5 using citric acid or monoethanolamine.

Example B1

5 mg of compound of formula (101) according to example A1 is dissolved in 20 g ethanol and then 30 g water is added:

This blue dyeing solution is applied on the dry hair (two blond, two middle blond and two damaged hair strands) and allowed to stand for 20 min. at room temperature.

Then the strands are rinsed under tap water and dried 12 hours.

Washing fastness: 10× washed with shampoo.

| Results: | | |
|---|---|---|
| Strand | Colour result | Washing fastness |
| blond | blue/good | 2-3 |
| middelblond | blue/good | 3-4 |
| damaged | blue/good | 3 |

Example B2

The 0.1%, by weight colouring material solution of example B1 is applied on the dry hair (two blond, two middle blond, and two damaged hair strands) and allowed to stand for 20 min. at room temperature.

Then the strands are rinsed and the towel dry strands are treated with the solution 2 (permanent fixation) and allowed to stand for 10 min.

Then the strands are rinsed under tap water and dried 12 hours at room temperature.

Washing fastness: 10× washed with shampoo.

| Results: | | |
|---|---|---|
| Strand | Colour result | Washing fastness |
| blond | blue/good | 2-3 |
| middelblond | blue/good | 3-4 |
| damaged | blue/good | 3 |

Example B3

A solution 1 (permanent lotion) is applied on shampooed hair (two blond, two middle blond, and two damaged hair strands) and allowed to stand for 10 min.

Then the strands are rinsed under tap water and the towel dry strands are treated with the 0.1%, by weight colouring material solution of example B1 allowed to stand for 20 min and then rinsed.

Then the towel dry strands are treated with the solution 2 (permanent fixation) and allowed to stand for 10 min.

Then the strands are rinsed under tap water and dried 12 hours at room temperature.

Washing fastness: 10× washed with shampoo.

| Results: | | |
|---|---|---|
| Strand | Colour | Washing fastness |
| blond | blue/good | 3-4 |
| middelblond | blue/good | 3-4 |
| damaged | blue/good | 2-3 |

The invention claimed is:

1. Dyes of formula

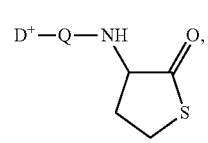

wherein

D is the radical of anthraquinone, acridine, azo, azomethine, hydrazomethine, benzodifuranone, coumarine, diketopyrrolopyrrol, dioxaxine, diphenylmethane, formazane, indigoid, indophenol, naphtalimide, naphthaquinone, nitroaryl, merocyanine, methine, oxazine, perinone, perylene, pyrenequinone, phtalocyanine, phenazine, quinoneimine, quinacridone, quinophtalone, stilbene, styryl, triphenylmethane, xanthene, thiazine dye and thioxanthene dye;

Q is $C_1$-$C_{30}$alkylene, —$C_2$-$C_{12}$alkenylene, —$C_5$-$C_{10}$arylene-, —$C_5$-$C_{10}$cycloalkylene- or —$C_1$-$C_{10}$alkylene($C_5$-$C_{10}$arylene)- which may be interrupted and/or terminated at one or both ends by one or more than one —O—, —S—, —N=, —N($R_1$)—, $SO_2$, —($CH_2CH_2$—O)$_{1-5}$—, —($CH_2CH_2CH_2$—O)$_{1-5}$—, —C(O)—$C_1$-$C_{12}$alkenylene, —C(O)O—, —OCO—,

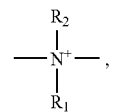

—CON($R_1$)—, —C(N$R_1R_2$)$_2$—, —($R_1$)NC(O)—, —CS$R_1$— or an optionally substituted, saturated or unsaturated, fused or non-fused aromatic or nonaromatic (hetero) cyclic) bivalent radical optionally comprising at least one heteroatom; —O—; —S—; —N($R_1$—; $SO_2$; —($CH_2CH_2$—O)$_{1-5}$; —C(O)—; —C(O)—$C_1$-$C_{12}$alkenylene; —C(O)O—, —OCO—;

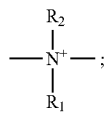

—CON($R_1$)—; —C(N$R_1R_2$)$_2$—; —($R_1$)NC(O)—; CS$R_1$; saturated or unsaturated, fused or non-fused aromatic or non-aromatic bivalent radical optionally comprising at least one heteroatom; which is optionally substituted by $C_1$-$C_{30}$alkyl, $C_1$-$C_{30}$alkoxy, $C_2$-$C_{12}$alkenyl, $C_5$-$C_{10}$aryl, $C_5$-$C_{10}$cycloalkyl, $C_1$-$C_{10}$alkyl($C_5$-$C_{10}$arylene), hydroxy or $D^+$;

$R_1$ and $R_2$ independently from each other are hydrogen; or unsubstituted or substituted, straight-chain or branched, monocyclic or polycyclic, interrupted or uninterrupted $C_1$-$C_{14}$alkyl; $C_1$-$C_{14}$ hydroxyalkyl; $C_1$-$C_{14}$ aminoalkyl; $C_2$-$C_{14}$alkenyl; $C_6$-$C_{10}$aryl; $C_6$-$C_{10}$aryl-$C_1$-$C_{10}$alkyl; or $C_5$-$C_{10}$ alkyl($C_5$-$C_{10}$aryl).

2. Dyes according to claim 1, wherein in formula (I)

D is the radical of anthraquinone, acridine, azo, azomethine, hydrazomethine, benzodifuranone, coumarine, diketopyrrolopyrrol, dioxaxine, diphenylmethane, formazane, indigoid, indophenol, naphtalimide, naphthaquinone, nitroaryl, merocyanine, methine, oxazine, perinone, perylene, pyrenequinone, phtalocyanine, phenazine, quinoneimine, quinacridone, quinophtalone, stilbene, styryl, triphenylmethane, xanthene, thiazine dye and thioxanthene dye;

Q is —$C_2$-$C_{12}$alkenylene, —$C_8$-$C_{10}$arylene-, —$C_8$-$C_{10}$cycloalkylene- or —$C_1$-$C_{10}$alkylene($C_8$-$C_{10}$arylene)- which may be interrupted by one or more than one —O—, —S—, —N$R_3$— or SO$_2$; —(CH$_2$CH$_2$—O)$_{1-5}$—; —C(O)—; —C(O)—$C_1$-$C_{12}$alkenylene; —C(O)O—; —OCO—;

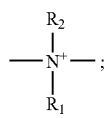

—N($R_1$)—; —CON($R_1$)—; —C(N$R_1R_2$)$_2$; —($R_1$)NC(O)—; —CS$R_1$—; —O—; —S—; —CS—; —S(O)—; or —S(O)$_2$—; and $R_1$, $R_2$ and $R_3$ independently from each other are hydrogen; unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl).

3. Dyes according to claim 1, wherein

D is selected from a nitroaryl, an anthraquinone, a naphthoquinone, a pyrenequinone, a phathylocyanine, a formazane, a methine, an azomethine, a dioxazine, a phenazine, an azo, an indophenol, a stilbene, a triphenylmethane, a xanthene, a thioxanthene and a direct dye.

4. Dyes according to claim 1, wherein D is a radical of formula (1a)

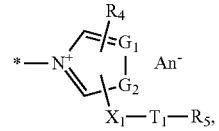

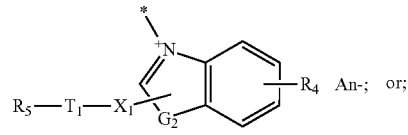

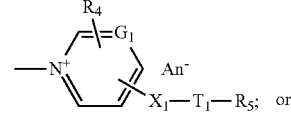

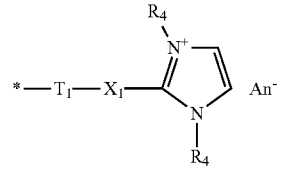

$X_1$ is a bivalent radical selected from —N=N—; —C$R_8$=N—; —N=C$R_8$—; —N$R_8$—N=C$R_9$—; and —$R_8$C=N—N$R_9$—;

$T_1$ is a bivalent radical of a substituted or unsubstituted aromatic or heteroaromatic compound;

$G_1$ is N; or a radical C$R_{10}$;

$G_2$ is —O—; or —S—;

$R_4$ and $R_5$ independently from each other are hydrogen; halogen; $C_1$-$C_{16}$alkyl, which may be interrupted with heteroatoms; phenyl; a carboxylic acid radical; a sulfonic acid radical; hydroxy; nitrile; $C_1$-$C_{16}$alkoxy; (poly)-hydroxy-$C_2$-$C_4$-alkoxy; halogen; SO$_2$N$R_6R_7$; S$R_6$; N$R_6R_7$; O$R_6$; SO$_2$; COO$R_6$; N$R_6$CO$R_7$; or CON$R_6$;

$R_6$ and $R_7$ independently from each other are hydrogen; $C_1$-$C_{12}$alkyl, which may be substituted by one or more $C_1$-$C_5$alkyl, $C_1$-$C_5$-alkoxy or hydroxyl; —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —NH$_2$, mono-$C_1$-$C_5$alkylamino, di-$C_1$-$C_5$alkylamino, —NO$_2$, carboxy or hydroxy;

$R_8$ and $R_9$ independently from each other are hydrogen; $C_1$-$C_{14}$alkyl; $C_2$-$C_{14}$alkenyl; $C_5$-$C_{10}$aryl; $C_1$-$C_{10}$alkyl-$C_5$-$C_{10}$aryl; or $C_5$-$C_{10}$aryl-$C_1$-$C_{10}$alkyl;

$R_{10}$ is hydrogen; $C_2$-$C_{14}$alkyl; $C_2$-$C_{14}$alkenyl; $C_6$-$C_{10}$aryl; $C_5$-$C_{10}$aryl-($C_1$-$C_{10}$alkyl); or —$C_1$-$C_{10}$alkyl($C_5$-$C_{10}$aryl); and An is an anion.

5. Dyes according to claim 1, wherein D is a radical of (1a1)

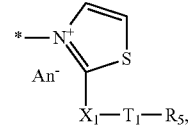

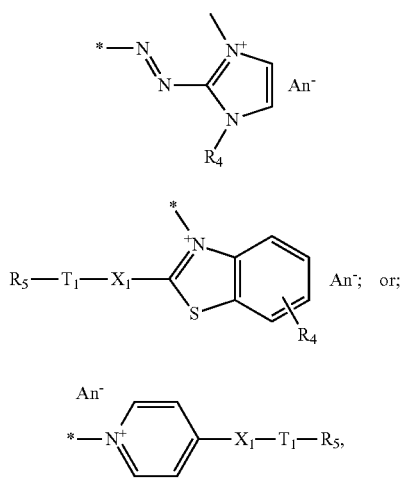

wherein

X₁, T₁ R₄, R₅ and An are

X₁ is a bivalent radical selected from —N=N—; —CR₈=N—; —N=CR₈—; —NR₈—N=CR₉—; and —R₈C=N—NR₉—;

T₁ is a bivalent radical of a substituted or unsubstituted aromatic or heteroaromatic compound;

R₆ and R₇ independently from each other are hydrogen; C₁-C₁₂alkyl, which may be substituted by one or more C₁-C₅alkyl, C₁-C₅-alkoxy or hydroxyl; —(CO)—H; —(CO)—C₁-C₅alkyl; phenyl or phenyl-C₁-C₄alkyl, wherein the phenyl moiety may be substituted by one or more C₁-C₅alkyl, C₁-C₅alkoxy, halogen, —NH₂, mono-C₁-C₅alkylamino, di-C₁-C₅alkylamino, —NO₂, carboxy or hydroxy;

An is an anion.

6. Dyes according to claim 1, wherein

Q is a bivalent radical of formula (1a) -(T)ₜ(Z)ᵤ—,

T is a radical selected from saturated or unsaturated, linear or branched —C₁-C₁₂alkylene; —C(O)—; —(CH₂CH₂—O)₁₋₅—; —(CH₂CH₂CH₂—O)₁₋₅—; —C(O)O—; —OC(O)—; —N(R₁)—; —CON(R₁)—; —(R₁)NC(O)—; —O—; —S—; —S(O)—; —S(O)₂—; —S(O)₂—N(R₁)—; and —N⁺(R₁)(R₂)—;

Z is —(CH₂)₂—SO₂—; —CH₂—CHR—CO—NR'—; or a biradical of formula (1b)

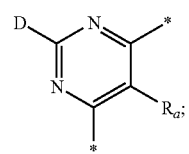

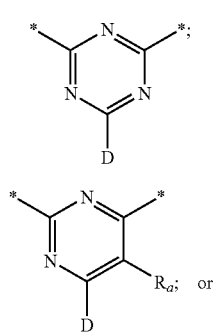

R and R' independently from each other are hydrogen; or C₁-C₆ alkyl;

D is Rₐ; D₁ᵃ⁺; or D₂ᵇ⁺;

a and b independently from each other are 1, 2 or 3;

Rₐ is chlorine or fluorine,

R₁ is unsubstituted or substituted C₁-C₆-alkoxy, C₁-C₆-alkylamino, C₆-C₁₀-aryloxy or C₆-C₁₀-aryl-amino; and t and z, independently from each other are 0; or 1; with the proviso that at least one of t or z is 1.

7. Dyes according to claim 5, wherein

X₁ is a bivalent radical selected from —N=N—; —CR₈=N—; and —N=CR₈—;

T₁ is phenylene;

R₅ is NR₆R₇; OR₆; or SO₂;

R₆ and R₇ independently from each other are hydrogen; or C₁-C₁₂alkyl, which may be substituted by one or more hydroxyl; and R₈ is hydrogen; or C₁-C₁₄alkyl.

8. Dyes according to claim 1, which correspond to formula

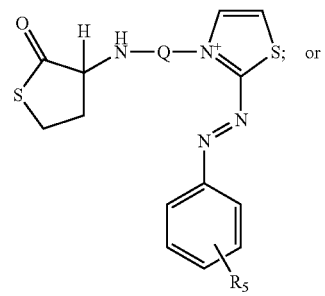

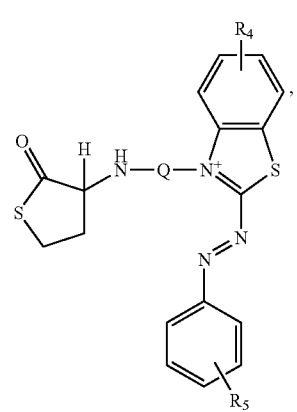

wherein

Q is C₁-C₃₀alkylene; C₂-C₁₂alkenylene, —C₅-C₁₀arylene-, —C(O)—; or —C(O)—C₂-C₁₂alkenylene;

R₄ is hydrogen; C₁-C₁₆alkyl; or C₁-C₁₆alkoxy;

R₅ is NR₆R₇; and

R₆ and R₇ independently from each other are hydrogen; or C₁-C₁₂alkyl, which may be substituted by one or more hydroxyl.

9. Dyes according to claim 5, which correspond to formula

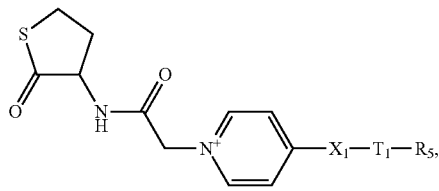

(3)

wherein $T_1$ is the same as defined in claim 5;

$X_1$ is a bivalent radical selected from —N═N—; —CR$_8$═N—;

$R_5$ is NR$_6$R$_7$; and $R_6$ and $R_7$ from each other are hydrogen; $C_1$-$C_{12}$alkyl; or phenyl; and $R_8$ is hydrogen; or $C_1$-$C_{14}$alkyl.

10. Dyes according to claim 1, which correspond to formula

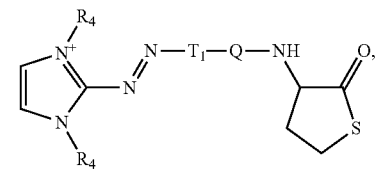

(4)

wherein $T_1$ is a bivalent radical of a substituted or unsubstituted aromatic compound;

Q is —$C_2$-$C_{12}$alkylene, which may be interrupted by one or more than one —NR$_3$—;

$R_3$ is hydrogen; or $C_1$-$C_{14}$alkyl; and $R_4$ is hydrogen; or $C_1$-$C_{16}$alkyl.

11. A method of dyeing keratin-containing fibers comprising treating the fiber with a dye as defined in claim 1.

12. A method according to claim 11, wherein the dyeing is carried out in presence of a reducing agent.

13. A method of dyeing keratin-containing fibers comprising treating the fiber with a dye as defined in claim 1 in the presence of a reducing agent, wherein the reducing agent is selected from thioglycol acid or salts thereof, gycerine monothioglycolate, cystein, 2-mercaptopropionic acid, 2-mercaptoethylamine, thiolactic acid, thioglycerine, sodium sulfite, dithionithe, ammonium sulfite, sodium bisulfite, sodium metabisulfite and hydrochinon.

14. A method according to claim 11, comprising treating the keratin-containing fiber (a) optionally with a reduction agent, and (b) with a dye as defined in claim 1, and (c) optionally with an oxidizing agent.

15. A composition comprising a dye as defined in claim 1.

16. A composition according to claim 15 in form of a shampoo, conditioner, gel or emulsion.

17. A composition according to claim 15 further comprising a direct dye and/or a reactive dye.

* * * * *